United States Patent [19]

Wisotzki et al.

[11] Patent Number: 4,852,591
[45] Date of Patent: Aug. 1, 1989

[54] APPARATUS FOR THE CARE OF CONTACT LENSES

[75] Inventors: Klaus-Dieter Wisotzki, Erkrath; Udo Schaab, Korschenbroich; Hans-Joachim Reitz, Roesrath; Jüergen Orczech, Ebersberg, all of Fed. Rep. of Germany

[73] Assignee: Henkel Kommanditgesellschaft auf Aktien, Duesseldorf, Fed. Rep. of Germany

[21] Appl. No.: 69,664

[22] Filed: Jul. 6, 1987

[30] Foreign Application Priority Data

Jul. 3, 1986 [DE] Fed. Rep. of Germany ....... 3622391

[51] Int. Cl.$^4$ .............................................. B08B 3/04
[52] U.S. Cl. .................................... 134/57 R; 134/93; 134/105; 134/113; 134/158; 134/188; 134/189; 134/192; 366/279; 366/331
[58] Field of Search ...................... 134/57 R, 58 R, 93, 134/105, 113, 158, 159, 186, 187, 188, 189, 192; 206/5.1; 366/279, 282, 331; 422/300, 307, 310

[56] References Cited

U.S. PATENT DOCUMENTS

| | | | |
|---|---|---|---|
| 3,586,012 | 6/1971 | Paule | 206/5.1 X |
| 3,614,959 | 10/1971 | Schollmaier et al. | 206/5.1 X |
| 3,621,855 | 11/1971 | Rabinowitz | 206/5.1 X |
| 3,623,492 | 11/1971 | Frantz et al. | 132/143 |
| 3,640,294 | 2/1972 | Piccolo | 206/5.1 X |
| 4,009,777 | 3/1977 | Thomas | 206/5.1 |
| 4,256,952 | 3/1981 | Thomas et al. | 219/521 |
| 4,270,309 | 6/1981 | Baumann | 47/59 |
| 4,369,355 | 1/1983 | Helixon | 219/521 |
| 4,396,583 | 8/1983 | Le Boeuf | 206/5.1 X |
| 4,444,307 | 4/1984 | Jermyn | 206/5.1 |
| 4,637,919 | 1/1987 | Ryder et al. | 422/300 |

FOREIGN PATENT DOCUMENTS

| | | |
|---|---|---|
| 21828 | 1/1981 | European Pat. Off. . |
| 31152 | 7/1981 | European Pat. Off. . |
| 2507353 | 9/1976 | Fed. Rep. of Germany . |
| 2925750 | 6/1981 | Fed. Rep. of Germany . |
| 3106519 | 10/1982 | Fed. Rep. of Germany . |
| 3145468 | 5/1983 | Fed. Rep. of Germany . |
| 3410400 | 9/1985 | Fed. Rep. of Germany . |
| 2072509 | 2/1981 | United Kingdom . |

Primary Examiner—Philip R. Coe
Attorney, Agent, or Firm—Ernest G. Szoke; Wayne C. Jaeschke; Henry E. Millson, Jr.

[57] ABSTRACT

A process and apparatus for the care of contact lenses in which the process comprises supporting contact lenses on a lens holder within a treatment container provided with a motor-driven stirrer and introducing into the container a liquid, e.g., salt water, and a two-component system including (1) a first component providing a peroxide-compound cleaning and sterilizing solution, preferably in solid form and (2) a second solid component containing a catalyst or reducing agent providing a neutralizing solution wherein the second component dissolution is delayed until after the first component has acted on the contact lenses, and wherein the action of both components is effected under stirring; and the apparatus for practicing this process comprises a housing, a treatment compartment in the housing to hold a liquid, a lens holder removably supported in the compartment, a stirrer movably positioned in the housing which is separate from the lens holder and which extends into the compartment and drive means to move the stirrer and agitate the liquid in the compartment.

15 Claims, 3 Drawing Sheets

APPARATUS FOR THE CARE OF CONTACT LENSES

BACKGROUND OF THE INVENTION

1. Field of the Invention

This invention relates to a process and apparatus for the care of contact lenses, wherein the lenses are treated in a liquid bath.

2 Description of Related Art

The increasing use of contact lenses has created an increasing demand for lens care processes that can be carried out by the contact lens user. Known processes for cleaning, disinfecting and sterilizing contact lenses which the user can perform at home or while traveling have the disadvantages of requiring relatively long treatment times of from twenty minutes to more than four hours, of exhibiting difficulty in handling the apparatus and/or of involving complicated procedures.

U.S. Pat. Nos. 4,009,777 and 4,444,307 and German Patent Publication No. OS 31 45 468, for example, describe containers for cleaning contact lenses comprising cup-like holders for the lenses that are usually mounted on a cover member. These containers differ from one another largely in the design of the cups and have the disadvantage that they do not include means for accelerating the cleaning process.

To accelerate the cleaning process, it is proposed in U.S. Pat. Nos. 4,256,952, 4,270,309 and 4,369,355, European Pat. No. 21 828 and British Patent No. 2,072,509, to provide contact lens containers with heating means. These containers employ temperatures of up to 100° C. in the liquid bath to sterilize the lenses. Containers employing these temperatures are not universally usable since such temperatures are suitable for so-called soft contact lens but not for so-called hard contact lens. In addition, with contact lens that have not been properly cleaned, high temperatures can result in deposits, particularly protein deposits, being fixed to the surface of lenses which makes cleaning more difficult.

Ultrasonic cleaning apparatus for contact lenses has also been provided as shown for example in German Patent Publication No. OS 29 25 750 and 05 31 06 519, in European Patent No. 31 152 and in UK Pat. No. 2,507,353. However, because of complicated and costly manufacture, ultrasonic cleaning apparatus is expensive and not easy to use at home or while traveling. In addition, the relatively severe mechanical stresses produced by ultrasonic treatment can damage the lenses.

U.S. Pat. No. 3,623,492 and German Patent Publication No. OS 34 10 400 describe contact lens cleaners comprising containers with lens holders designed to rotate in the cleaning solution and thus to promote washing of the cleaning liquid over the surfaces of the contact lens. In cleaners of these designs no Provision has been made for agitating the liquid bath to accelerate the dissolution of, for example, a tablet or a powder of a cleaning or sterilizing material. In addition, this type of cleaner is designed for manual use with the container covers being provided wit a rotatable portion connected to the contact lens holder so that, when the cover is turned, it rotates the lens holder. Since use of this arrangement is a very tiresome procedure, the cleaning cycle is apt to be stopped before the lenses are completely cleaned.

BRIEF DESCRIPTION OF THE DRAWINGS

The invention is hereinafter described with reference to the accompanying drawings, wherein.

DESCRIPTION OF THE INVENTION

Figure 1:
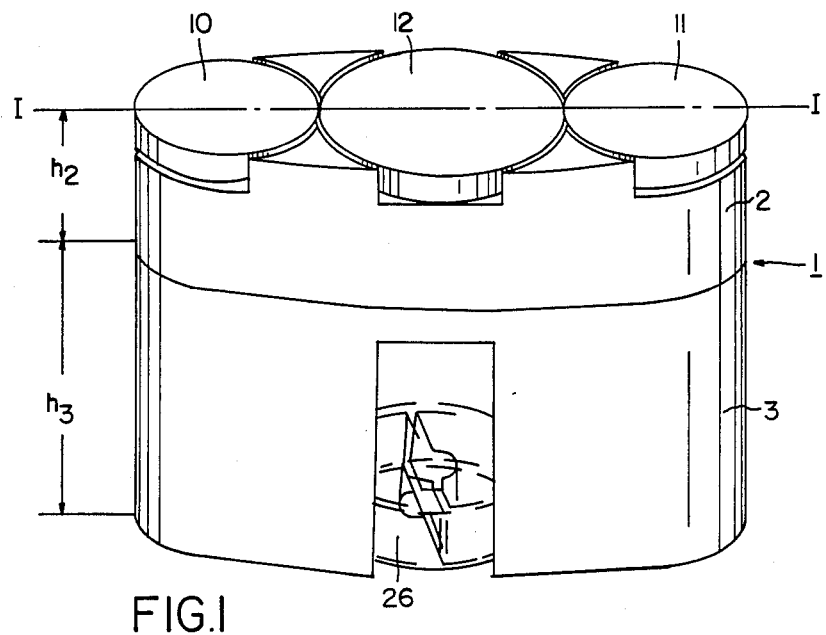
FIG. 1 is a perspective view of an apparatus according to this invention.

It is an object of the present invention to provide a method and apparatus for cleaning contact lenses which avoid the disadvantages of the prior art and which provide for simple and easy as well as more complete cleaning of the lenses, and which also are suitable for use while traveling.

This and other objects are achieved in accordance with this invention by providing a method in which two tablets or a tablet and a powder containing respectively a solid peroxide compound for sterilizing or disinfecting of the lenses and a catalyst and/or a reducing agent for neutralization of residual peroxide are introduced into a container in which there is disposed a motor-driven stirrer that is independent of the lens holder. The container is filled with a liquid such as a common aqueous salt solution or water, or optionally, distilled water, in which the contact lenses to be treated are immersed. The tablets and/or powders are adapted to be dissolved by stirring, the peroxide-containing compon%nt being designed to dissolve before the catalyst and/or reducing agent-containing component to form first a sterilizing and cleaning solution and then form a neutralizing solution.

By virtue of the method of this invention, it is necessary to prepare only a single cleaning bath for cleaning the contact lens in which the cleanin9 cycle is relatively short and, in addition, is safe and easy and convenient to use. Compared to conventional cleaning processes for contact lens which require treatment times of twenty minutes or more before the contact lens are substantially ready for use again, the entire sterilizing, cleaning and neutralizing treatment in the process of the present invention requires generally about ten minutes.

Through the use of tablets or powders that are dissolved in the liquid, and the use of stirring, the contact lens also are cleaned more thoroughly and effectively.

In accordance with an alternate embodiment of this invention, the sterilizing and cleaning compound can be introduced as a ready-to-use sterilizing and/or cleaning liquid in which the materials, particularly peroxide compounds, have already been dissolved. The advantage of this over the use of tablets and/or powder is that, with less solid material to be dissolved, the cycle time as well a the volume of the material to be dissolved in the container can be reduced.

The process of this invention may further be accelerated by heating the liquid in the container preferably to a temperature of not more than 60° C. and preferably to a temperature of about 35° C. A temperature of this order accelerates the dissolution of the materials as well as the cleaning and sterilizing process, but is still considerably below the temperature at which even heat sensitive contact lenses are likely to be damaged.

According to another embodiment of the method of this invention a tablet containing additives that change the color of the liquid upon completion of the sterilizing and cleaning process can be employed so that the user knows immediately when the cleaning process is completed and the neutralizing process has started.

Also in accordance with this invention, a treatment liquid, that is the salt solution or distilled water, can be introduced into the container under pressure such as from pressurized dispenser such as a spray bottle or aerosol can, which is a convenient way for the solutions to be stored and handled while traveling.

The apparatus in accordance with this invention includes a housing in which there is arranqed a motor, a drive unit, a stirrer, a contact lens holder, a compartment for the liquid bath and a power supply unit. The apparatus is easy and convenient to use as well as relatively fast, safe and reliable. The apparatus does not require an outside source to power, and is adapted to be made relatively small and flat and thus is convenient to carry in a handbag or jacket pocket or the like for use while traveling.

In one preferred embodiment of the apparatus according to the invention the compartment for the liquid bath is positioned between the compartment for the motor and the compartment for the power supply unit, and the apparatus further includes removal openings for the power supply unit and the contact lens holder and a switch for operating the stirring mechanism.

In another embodiment of the apparatus, which has the advantage of being inexpensive to manufacture, the compartments for accommodating the motor, the power supply unit and the liquid bath are positioned in a lower part of the apparatus while the removal openings for the power supply unit and the contact lens holder, the switch and receiving grooves for the stirrer and a transmission assembly are positioned in an upper part of the apparatus whereby the upper part is placed on top of the lower part to form a housing.

The apparatus according to the present invention is further distinquished bY a stirrer which is rotatably mounted in qrooves in the housinq and operatively connected by a transmission to the motor, and which stirrer extends downwardly to near the bottom of the compartment for the liquid bath. Such a stirrer accelerates the dissolution of powders or tablets used in the cleaning of contact lenses through agitation of the bath.

In a preferred embodiment, the apparatus of this invention includes a cylindrical stirrer provided at its upper end with an annular gear and at its lower end, with a plurality of depending vanes adapted to create an upwardly directed flow component in the liquid bath.

In another embodiment of the invention, the stirrer is provided with sealing means to seal off the motor and power supply unit compartments against the entry of liquid from the liquid bath compartment.

According to another aspect of the invention, there is provided a transparent container which forms the compartment for the liquid bath and which is removably connected to the apparatus to enable any change of color of the liquid bath to be clearly observed and to enable the compartment for the liquid bath to be removed for cleaning.

To enable the apparatus according to the invention to be filled from spray cans, for example aerosol cans, the compartment for the liquid bath or the container can include a filling valve.

In another embodiment of the invention, a heating element is provided to heat the liquid bath, e.g., to a temperature of less than or equal to 60° C. and preferably to a temperature of about 35° C.

To enable the contact lenses and a dissolvable cleaning tablet to be readily immersed in the liquid bath, the apparatus according to this invention can be provided with a holding means adapted to receive both the contact lenses and the cleaning tablet. This holding means can comprise a strip of polytetrafluoroethylene which is provided with openings to receive the contact lenses and further adapted to act as a carrier for a cleaning tablet.

Since an excess pressure can develop in the last phase of the cleaning process, i.e., the neutralization step, the apparatus of the present invention may be provided with a pressure relieving safety valve to prevent destruction of the apparatus.

To make it easier and more safe to handle, the apparatus according to this invention can be provided with means which visually and/or acoustically indicate the end of the treatment process and a lock which prevents the container from being opened while the stirrer is running.

In another embodiment of the invention, the apparatus according to the present invention is provided with electronic controls which are operatively connected to the motor and optionally to the heating element, these controls indicating the end of the treatment process arm controlling the anti-opening lock. These controls are preferably located in the motor compartment.

Finally, another embodiment of the apparatus according to this invention is characterized in that the ratio to the height of the lower part to the height of the upper part is approximately 4 5:2. This ratio enables a compact construction employing standard commercial batteries (power source), switches and motors which may be conveniently carried while traveling for example in a handbag.

Figure 2:
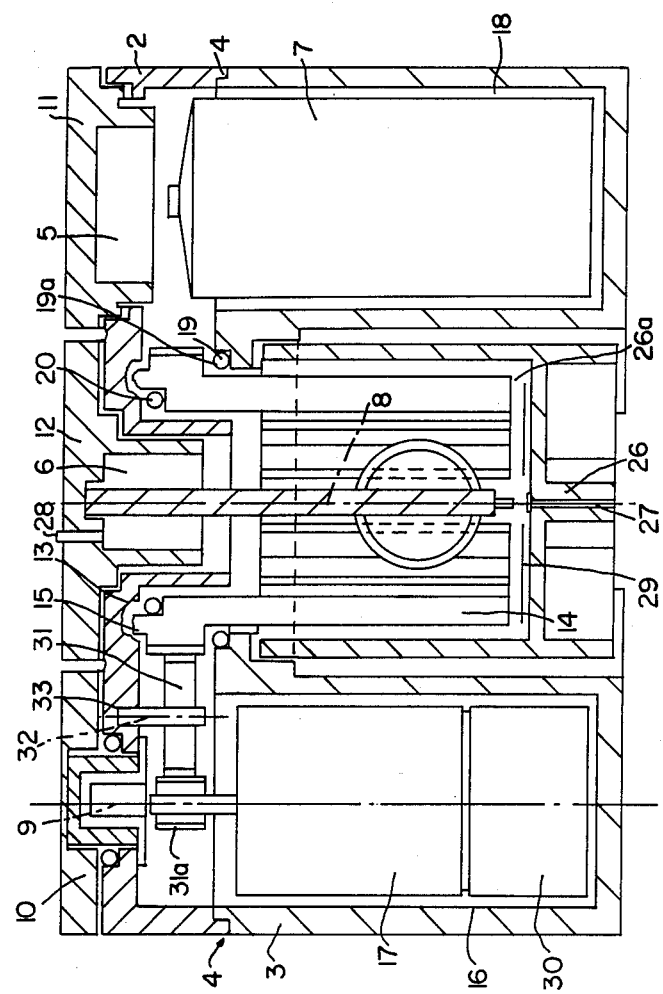
FIG. 2 is a sectional view through the apparatus substantially on the line I—I of FIG. 1.

FIG. 1 shows a housing 1 that is generally elliptical in cross section. Housing 1 consists of an upper part 2 and a lower part 3 which are held firmly together by deformable latch means 4 (see FIG. 2) formed around the meeting edges at the bottom and top respectively of parts 2 and 3.

Upper part 2 includes openings 5 and 6 through which a power supply unit 7 and a contact lens holder 8 are inserted into and removed from housing 1. A rotary switch 10 is mounted in another opening 9 in upper part 2. As shown, openings 5, 6, and 9 are aligned lengthwise of the unit with opening 5 for the power-supply unit and opening 9 for rotary switch 10 being disposed on opposite sides of central opening 6 for lens holder 8. Opening 5 is closed by a cover 11 while opening 6 is closed by a cover 12 to which contact lens holder 8 is secured and from which it depends. Covers 11 and 12 are threaded into the openings 5 and 6 respectively.

A stirrer 14 extends into lower part 3 and is rotatably supported at its upper end by a web 15 having an upper end received in an annular clearance groove 13 in upper part 2. An external ledge 19a of web 15 is supported on a bearing ring 19 in the form of an O-ring that, in turn, rests on a ledge on lower part 3. Web 15 provides a seal between upper part 2 and lower part 3 to seal off a motor compartment 16 in lower part 3 beneath opening 9 for a motor 17 and a power supply compartment 18 in lower part 3 beneath opening 5 for the power supply unit which, as shown, comprises a battery 7. The seal comprises bearing ring 19 and a similar bearing ring 20 between ledge 15a (FIG. 3) on the top of web 15 and an opposed surface on the underside of upper part 2 around groove 13.

A container 26 forming a treatment compartment 26a for the liquid is situated as shown between compartments 16 and 18. In the illustrated embodiment, container 26 is transparent and is provided with external threads about the upper edge thereof that are adapted to be threaded into cooperating threads in lower part 3, although it could also be integral with lower part 3.

In the base of container 26, there is a filling valve 27 for filling container 26 with liquids under pressure from a supply container, such as an aerosol can. A safety valve 28 is provided in cover 12 to relieve pressure in container 26 generated during filling or generated by the decomposition of excess peroxide after the cleaning process is completed.

Figure 4:
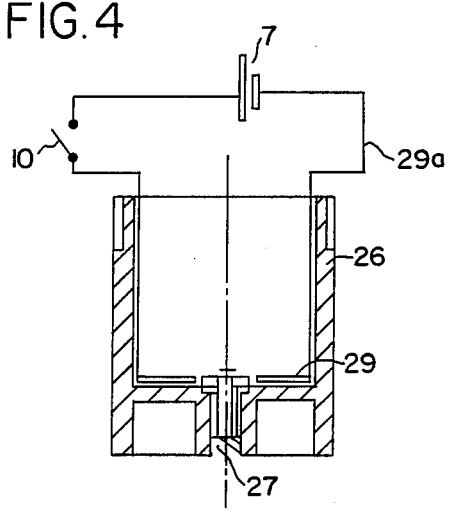
FIG. 4 is a vertical sectional view of the container for the liquid bath of the apparatus of FIG. 1.

A heating element 29 is positioned at the base of container 26 and is connected by leads 29a (shown diagrammatically in FIG. 4) to power supply unit 7 and to rotary switch 10. The leads may be formed either by printed metallic conductors on the housing or by standard wires. Heating element 29 is designed in such a way that liquid in compartment 26a is heated to at most 60° C. and preferably only to about 35° C. Heaing element 29 may be an electrical resistance heating element in the form of a plate, coil or wire or may be integrated in the walls of the container 26 or in stirrer 14.

Electronic controls 30 are positioned under motor 17 in motor compartment 16 and cooperate with the motor 17 and, optionally, with heating element 29 in such a way that, after a certain period of time, the flow of current to the motor and to the heating element is interrupted so that the apparatus is switched off.

The apparatus and, in particular, the rotating stirrer may be switched on and off at any time using rotary switch 10 independently of electronic controls 30.

In the embodiment shown, motor 17 may be a standard commercial series motor, for example, with an operating voltage of 1.5 volts and approximate dimensions of 25 mm (diameter) and 25 to 40 mm (height).

Power supply unit 7 is a standard commercial battery but it may also be a rechargeable battery, a power pack or a connector to a powerpack.

A transmission unit in the form of a gear 31 is positioned in upper part 2 to drive stirrer 14 and to connect stirrer 14 to motor 17. Transmission unit 31 can be journaled, for example, for rotation on a shaft J2 mounted in an opening 33 in upper part 2.

Figure 3:
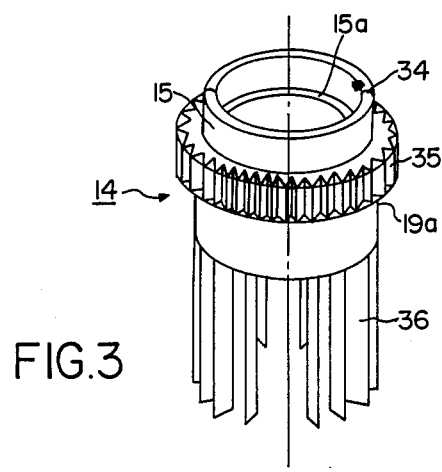
FIG. 3 is a perspective view of the stirrer of the apparatus of FIG. 1.

Stirrer 14, which is shown in more detail in Figure 3, consists of a cylindrical body 34, formed integrally at its upper end with an annular gear 35 which meshes with gear 31. Gear 31 also meshes with a gear 31a on the output shaft of motor 17. At its lower end, body 34 is provided with a plurality of depending vanes 36, that are disposed relatively close to the side walls of container 26, extend close to the bottom thereof and are oriented so that when stirrer 14 is rotated, the liquid bath in chamber 26a is agitated and is given, at least in part, an upwardly directed flow component.

In the illustrated embodiment of the invention the volume of compartment 26a is preferably about 10 ml.

Figure 5:
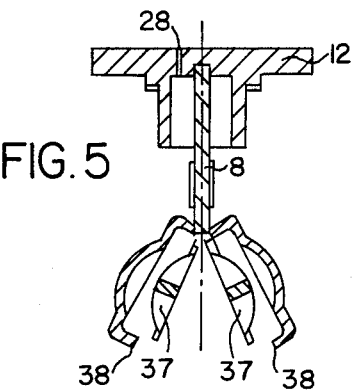
FIG. 5 is a vertical sectional view of the contact lens holder of the apparatus in FIG. 1.

Contact lens holder 8 in partly open form is shown in detail in FIG. 5. Holder 8 includes a carrier 37 and contact lens cups 38. Carrier 37 is designed to be opened like a clam shell to receive the cleaning and sterilizing material and the neutralizing material in a solid form such as tablets or powders to be dissolved in the treatment liquid. Contact lens cups 38 are also designed to be opened like a clam shell about a hinge above the hinge of carrier 37 and to receive the contact lenses to be cleaned and to enclose carrier 37 in the closed position. Cups 38 are arranged on contact lens holder 8 so as to be immersed in the liquid bath in compartment 26a. In use, carrier 37 is closed to hold the tablet or powder and to provide convex outer surfaces that receive the contact lenses to be cleaned. Contact lens cups 38 are then closed over carrier 37 to confine the contact lenses.

Figure 6:
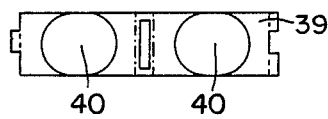
FIG. 6 is a plan view of a strip with contact lens cups adapted for use in accordance with an alternative embodiment of the invention.

In FIG. 6 there is shown a strip 39 that may be formed of polytetrafluoroethylene for example and provided with sieve-like openings 40 to receive the contact lenses to be cleaned and which may be attached to contact lens holder 8 as an alternative to contact lens cups 38.

There may also be provided a lock (not shown) to prevent the apparatus from being opened before the treatment is completed and means for generating a signal (not shown) that may be seen and/or heard by the user to indicate the end of the treatment cycle or the completion of different phases of the treatment cycle. Means such as these are readily available and will be obvious to those skilled in the art. For example, the lock may be mechanical, electrical or magnetic. The signal may be, for example, an additive to the liquid bath to change the color of the bath, which is visible through a window 3a in lower part 3. Tartrazines, riboflavin, fluorescein and vitamin B12 are examples of additives which may be used to cause a change in the color of the liquid bath on completion of the sterilizing and cleaning process. Bulbs or light emitting diodes which are energized at the end of the treatment process also may be used. The individual steps of the treatment process (cleaning, sterilizing, neutralizing) could also be indicated by further light emitting diodes.

Insofar as possible, the components of the apparatus are preferably fabricated from a plastic resistant to the peroxide-containing solution. The height $h_2$ of upper part 2 is preferably from about 22.5 to about 27.5 mm while the height $h_3$ of lower part 3 is preferably from about 45 to 55 mm.

The embodiment described in the foregoing may of course be modified in several respects without departing from the basic concept of the invention. For example, upper part 2 and lower part 3 may be bonded to one another. In addition, the rotary switch establishing the electrical connections between the power supply unit and the motor and heating element may be in the form of a push button switch or a sensor switch.

It is also possible to provide the contact lens cups with markings, for example, L and R, to clearly identify the contact lens placed therein.

In addition, rather than being closed within the contact lens cups 38 and opening like a clam shell, carrier 37 for the cleaning tablets may comprise for example a star-shaped carrier disposed beneath the contact lens cups.

The process according to the invention is carried out, for example, by introducing into apparatus 1 a single tablet of two materials that will dissolve at different rates, or two tablets, or a tablet and a powder or a tablet and a sterilizing solution respectively containing the components as described above. Those skilled in the art can readily provide tablets or powders with coatings or with different densities or binders to insure that the product containing the peroxide compound will be dissolved first and, after a predetermined time interval, the product containing the catalysts and/or reducing agent will be dissolved. Use of the tablets or powders with suitable liquids, particularly a common salt solution or distilled water, produces a lens cleaning liquid bath that changes from a sterilizing and cleaning solution into a neutralizing solution.

Although certain embodiments of the invention have been described in detail, it will be appreciated that other embodiments are contemplated along with modifications of the disclosed features as being within the scope of the invention which is defined in the appended claims.

We claim:

1. An apparatus for the care of contact lenses comprising a housing, a treatment compartment in said housing for containing a liquid, a stirrer supported by said housing above said compartment for movement about a vertical axis extending substantially centrally of said compartment, said stirrer having stirring means extending into said compartment from an annular gear extending around the upper end of said stirrer above said treatment compartment, and drive means cooperating with said gear for imparting rotation to said stirrer to agitate liquid in said compartment with said stirring means, and a lens holder formed separately from said stirrer, said lens holder being removably supported in said housing and extending into said compartment.

2. An apparatus in accordance with claim 1 wherein said drive means includes an electrical motor supported in said housing and having a drive shaft coupled to said annular gear.

3. An apparatus in accordance with claim 1 in which said stirring means comprises a cylindrically arranged plurality of vanes depending into said compartment adjacent to the side walls thereof and extending substantially to the bottom thereof, said lens holder being disposed internally of said vanes in said compartment.

4. An apparatus in accordance with claim 1, wherein said lens holder includes a carrier for materials adapted to be dissolved in the liquid in said treatment compartment.

5. An apparatus in accordance with claim 4 in which said carrier is disposed internally of said lens holder.

6. An apparatus in accordance with claim 5 in which said lens holder and said carriers are each adapted to be opened and closed about hinge means.

7. An apparatus for the care of contact lenses comprising a housing which is substantially flat and, a treatment compartment disposed centrally of said housing for containing a liquid, said housing includes a power supply compartment and a motor compartment on opposite sides of said treatment compartment, a stirrer movably held in said housing and having stirring means extending into said treatment compartment, a lens holder formed separately from said stirrer, said lens holder being removably supported in said housing and extending into said treatment compartment, and drive means including a motor in said motor compartment to move said stirrer and agitate liquid in said treatment compartment with said stirring means.

8. An apparatus in accordance with claim 7 in which said power supply compartment is open at the top of said housing for introducing and removing a battery means and adapted to be closed by cover means, and further including switch means mounted on said housing above said motor compartment, 9. An apparatus in accordance with claim 7 having electronic controls for controlling said motor, said controls being disposed in said motor compartment, and switch means for energizing said electronic controls.

10. An apparatus in accordance with claim 7 having heater means disposed in said treatment compartment and adapted to be energized by an electrical power source in said power supply compartment for heating the liquid therein.

11. An apparatus in accordance with claim 10 having electronic controls for controlling said motor and said heater, and switch means for energizing said electronic controls.

12. An apparatus in accordance with claim 7 in which said treatment compartment has a side wall and is of transparent material and said housing is provided with a window opposite the side wall of said treatment compartment whereby the solution in said treatment compartment is visible during the cleaning cycle.

13. An apparatus in accordance with claim 7 including seal means disposed around said stirrer for sealing off liquid communication between said treatment compartment and said motor and power supply compartments.

14. An apparatus in accordance with claim 13 wherein said stirring means extends from an annular gear extending around the upper end of said stirrer above said treatment compartment, and said seal means includes a first seal ring located below said gear and a second seal ring located radially inward of said gear and above said first seal ring.

15. An apparatus in accordance with claim 7 wherein said treatment and power supply compartments have open tops and cover means are provided for selectively opening and closing said open tops.

* * * * *